United States Patent [19]

Orr et al.

[11] 4,160,844

[45] Jul. 10, 1979

[54] COMPOSITION FOR TREATING SKIN MAST CELLS AND/OR DELAYED CELLULAR HYPERSENSITIVITY REACTIONS

[75] Inventors: Thomas S. C. Orr, Melton Mowbray; Raymond W. Keogh, East Goscote, both of England

[73] Assignee: Fisons Limited, London, England

[21] Appl. No.: 794,030

[22] Filed: May 5, 1977

[30] Foreign Application Priority Data

May 21, 1976 [GB] United Kingdom ............... 20986/76

[51] Int. Cl.$^2$ ..................... A61K 31/35; A61K 31/41; A61K 47/00

[52] U.S. Cl. ................................. 424/283; 424/258; 424/358; 424/359; 424/363; 424/365

[58] Field of Search ........................................ 424/283

[56] References Cited

FOREIGN PATENT DOCUMENTS 836121 5/1976 Belgium.

*Primary Examiner*—Donald B. Moyer
*Attorney, Agent, or Firm*—Merriam, Marshall & Bicknell

[57] ABSTRACT

There is described a pharmaceutical composition suitable for application to the skin and comprising, as active ingredient, a compound of formula I,

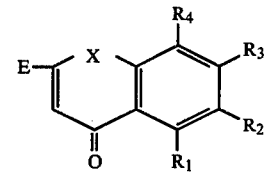

in which
  $R_1$ represents hydrogen, hydroxy or $-NR_5R_6$, in which $R_5$ and $R_6$, which may be the same or different, each represent hydrogen or alkyl C 1 to 6,
  an adjacent pair of $R_2$, $R_3$ and $R_4$ form a $-(CH_2)_4-$ chain, and the remaining substituent $R_2$ or $R_4$ represents alkyl C 1 to 9,
  E represents a 5-(1H)tetrazolyl- or a $-COOH$ group, and
  X represents oxygen or a group $-NR_7-$ in which $R_7$ may be hydrogen or alkyl C 1 to 6, or a pharmaceutically acceptable derivative thereof.

There is also described a method for the treatment of conditions (in man and other animals) which involve skin mast cells and/or delayed (cellular) hypersensitivity reactions, which comprises administering a compound of formula I, or a pharmaceutically acceptable derivative thereof to a subject suffering from such a condition.

13 Claims, No Drawings

COMPOSITION FOR TREATING SKIN MUST CELLS AND/OR DELAYED CELLULAR HYPERSENSITIVITY REACTIONS

This invention relates to a novel pharmaceutical formulation and to a new method of treatment.

According to the invention there is provided a pharmaceutical composition suitable for application to the skin and comprising, as active ingredient, a compound of formula I,

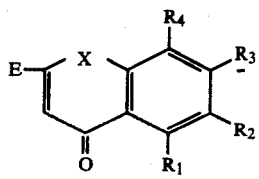

in which
- $R_1$ represents hydrogen, hydroxy or $-NR_5R_6$, in which $R_5$ and $R_6$, which may be the same or different, each represent hydrogen or alkyl C 1 to 6,
- an adjacent pair of $R_2$, $R_3$ and $R_4$ form a $-(CH_2)_4-$ chain, and the remaining substituent $R_2$ or $R_4$ represents alkyl C 1 to 9,
- E represents a 5-(IH)tetrazolyl— or a —COOH group, and
- X represents oxygen or a group $-NR_7-$ in which $R_7$ may be hydrogen or alkyl C 1 to 6, or a pharmaceutically acceptable derivative thereof.

Pharmaceutically acceptable derivatives of the compounds of formula I include pharmaceutically acceptable salts, and, when E is a —COOH group, esters and amides of the 2-carboxylic acid group. Suitable salts include ammonium, alkali metal (e.g., sodium, potassium and lithium) and alkaline earth metal salts (e.g. calcium or magnesium), and salts with suitable organic bases, e.g. salts with hydroxylamine, lower alkylamines such as methylamine or ethylamine, with substituted lower alkylamines, e.g. hydroxy substituted alkylamines such as tris(hydroxymethyl)methylamine, or with simple monocyclic nitrogen heterocyclic compounds, e.g. piperidine or morpholine. Suitable esters include simple lower alkyl (C 1 to 6) esters, e.g. the ethyl ester, esters derived from alcohols containing basic groups, e.g. di-lower alkyl amino substituted alkanols such as the β-(diethylamino)-ethyl ester, and acyloxy alkyl esters, e.g. a lower acyloxy-lower alkyl ester such as the pivaloyloxymethyl ester, or a bis-ester derived from a di-hydroxy compound, e.g. di(hydroxy-lower alkyl) ether, e.g. the bis-2-oxapropan-1,3-diyl ester. The pharmaceutically acceptable acid addition salts of the basic esters and of those compounds in which $R_1$ is a group $-NR_5R_6$, e.g. the hydrochloride, the hydrobromide, the oxalate, the maleate or the fumarate may also be used. The esters may be made by conventional techniques, e.g. esterification, transesterification or reaction of the acid, or a salt thereof, with an appropriate compound containing a good leaving group. The amides may be, for example, unsubstituted or mono- or di- C 1 to 6 alkyl amides and may be made by conventional techniques, e.g. reaction of an ester of the corresponding acid with ammonia or an appropriate amine. We prefer to use a free acid of formula I or a sodium salt thereof.

We prefer $R_5$ and $R_6$ to be selected from hydrogen and alkyl C 1 to 3, e.g. methyl or ethyl. We also prefer $R_1$ not to be hydrogen (e.g. to be —OH), $R_2$ and $R_3$ to together form the $-(CH_2)_4-$ chain, and $R_4$ to be alkyl C 2 to 4, e.g. propyl. $R_7$ is preferably C 1 to 4, e.g. ethyl, however we prefer X to be oxygen.

Specific compounds of formula I which may be mentioned are:
5-Amino-6,7,8,9-tetrahydro-4-oxo-10-propyl-4H-naphtho[2,3-b]-pyran-2-carboxylic acid,
6,7,8,9-Tetrahydro-5-hydroxy-4-oxo-10-propyl-4H-naphtho[2,3-b]-pyran-2-carboxylic acid,
5-Dimethylamino-6,7,8,9-tetrahydro-4-oxo-10-propyl-4H-naphtho[2,3-b]pyran-2-carboxylic acid,
7,8,9,10-Tetrahydro-5-hydroxy-4-oxo-6-propyl-4H-naphtho[1,2-b]pyran-2-carboxylic acid,
1-Ethyl-5-hydroxy-6-propyl-7,8,9,10-tetrahydro-4(1H)-benzo[h]-quinolinone-2-carboxylic acid,
5-(6,7,8,9-Tetrahydro-5-hydroxy-4-oxo-10-propyl-4H-naphtho[2,3-b]pyran-2-yl)tetrazole, and
6,7,8,9-Tetrahydro-4-oxo-10-propyl-4H-naphtho[2,3-b]-pyran-2-carboxylic acid.

The active ingredient may be applied topically to the skin tissues of the mammal, notably man, cat, dog or horse. Thus the active ingredient may be formulated as an ointment, in which the finely ground active ingredient is dispersed in a waxy, fatty, protein or paraffin base, especially a soft paraffin base. Liquid paraffin, hard paraffin, and wool fat may be included in the ointment base.

We prefer to use a composition containing a major proportion (e.g. 70–90% w/w) of a white or yellow soft paraffin and optionally minor proportions of a liquid paraffin (5–15% w/w) and of a hard paraffin (0–12% w/w).

The ointment may also contain other liquid components, e.g. water or a polyethylene glycol to improve the consistency of the base, provide a solvent for the active ingredient so that the active ingredient may be sterilised by filtration and/or to alter the rate of release of the active ingredient from the base.

The active ingredient may alternatively be formulated as a cream, which may be either an oil in water type, or a water in oil type. Suitable emulsifying agents for the former type include sodium, potassium, ammonium and triethanolamine soaps; polysorbates; and cationic, anionic, and non-ionic emulsifying waxes. Suitable emulsifying agents for the latter type include calcium soaps, wool fat, wool alcohols, beeswax, and certain sorbitan esters.

The ointment and cream compositions may if desired contain an effective proportion of a pharmaceutically acceptable preservative or sterilising agent suitable for an ointment or cream. Examples of preservatives which may be used are (i) Chlorbutol (2,2,2-trichloro-1,1-dimethyl ethanol hemihydrate), which may be present in the composition at about 0.5% w/w, (ii) Chlorocresol, which may be present in the composition from about 0.05% to 0.2% w/w, (iii) Methyl-p-hydroxybenzoate, either alone or in combination with propyl-p-hydroxybenzoate (the total concentration of hydroxybenzoate esters in the composition may range from about 0.08% to 0.2% w/w), and (iv) Thiomersal.

The active ingredient may alternatively be formulated as a lotion or liniment by dissolving or dispersing the compound in an aqueous or oily base. A suitable preservative may be included in the formulation. Ethanol and/or glycerin may be included in the aqueous base. Suitable solvents include glycols, e.g. propylene glycol or polyethylene glycol 200–700; alcohols, e.g. ethanol, isopropanol or glycerol; fixed oils, e.g. almond oil, arachis oil, caster oil, fractionated coconut oil, ethyl oleate, maize oil or olive oil; esters, e.g. isopropyl myristate, isopropyl linoleate; isopropyl palmitate or isopropyl palmitate-stearate; dimethyl sulphoxide; benzyl benzoate; or a mixture of two or more of the above solvents. Where pastes, gels or emulsions are desired, a thickening agent may be incorporated in an aqueous base. Suitable thickening agents include 'Carbopol' ('Carbopol' is a Trade Mark) which is a polymer of acrylic acid cross linked with allylsucrose, bentonite, soluble cellulose derivatives (e.g. sodium carboxy methyl cellulose, hydroxypropyl methyl cellulose), 'Veegum' or polyvinyl alcohol.

A particularly preferred composition according to the invention comprises a mixture of a solvent for the active ingredient and a non-solvent for the active ingredient, the solvent and the non-solvent being miscible in the relevant proportions and the proportion of the non-solvent being such that the active ingredient forms a saturated or near saturated solution in the mixture. The solvent may, for example, be a suitable organic solvent such as propylene glycol, and the non-solvent may be, for example, water. The mixture is desirably formulated as a gel, e.g. by the incorporation of a suitable thickening agent. Suitable thickening agents include those specified above and in particular 'Carbopol 934' which is a polymer of acrylic acid cross linked with allylsucrose. To produce a gel at least some of the carboxyl groups of the 'Carbopol' should be neutralised and we prefer to use an organic base, e.g. triethylamine or diisopropanolamine, which forms a salt with the 'Carbopol' which is compatible with the solvent system. It is desirable to control the pH of the mixture to ensure that as much as possible of the active ingredient is in the form (e.g. acid or salt) which is most readily absorbed by the skin, and that the mixture is saturated with the desired form of active ingredient. When a gel is used the pH should be adjusted to ensure that the gel has the desired viscosity. We prefer the compositions of the invention to have a pH in the range 4 to 6, and preferably about 5.

Other ingredients e.g. humectants, antioxidants, perfumes and pigments may also be present if desired.

The active ingredient may also be formulated as a dusting powder in which two or more ingredients are intimately mixed in fine powder form. Alternatively, the active ingredient may be applied as a solution or suspension in a liquid carrier to the surface of a solid carrier and the coated particles dried. Examples of solid carriers, which are normally sterilised, are talc, starch, lactose, zinc oxide, light kaolin and calcium carbonate.

A semi-solid base that has been found particularly suitable is based on a fatty alcohol/glycol mixture. Suitable fatty alcohols include saturated alkanols containing 16 to 24 carbon atoms and suitable glycols include 1,2-propylene glycol, 1,3-propylene glycol, polyethylene glycols of molecular weight 100 to 800, and dipropylene glycol. The fatty alcohol and glycol are present in from 15 to 45:45 to 85 parts by weight, preferably 20 to 35:55 to 80 parts, respectively. If desired a plasticizer, e.g. a polyethylene glycol of molecular weight 800 to 20,000 or 1,2,6-hexanetriol, and/or a penetrant may also be present.

The active ingredient may be present in the compositions of this invention in an amount of from 0.1 to 20%, preferably 0.1 to 10% and more preferably 0.3 to 5% by weight of the total composition.

Where solid particles of the active ingredient are present, e.g. in a suspension or dispersion or in a powder formulation, it is preferred that these have a mean particle size in the range 0.01 to 10 micrometers.

The compositions according to the invention may be made by mixing the ingredients, e.g. by dry mixing or by grinding the solid ingredients together, or by emulsifying an aqueous solution of the active ingredient with an appropriate oil base. To avoid precipitation of active ingredient during the preparation of a gelled mixed solvent product a solution of active ingredient in the solvent may be added to the non-solvent. The final pH of the formulation may be controlled by the addition of an appropriate quantity of acid or base.

The active ingredient is preferably administered to the skin of a patient merely by smearing or spreading a suitable composition, e.g. an ointment, cream or paste over the area of the skin affected or likely to be affected. Alternatively, the compound may be impregnated into a gauze or similar pad and this pad then applied to the affected area; or a powder containing the active ingredient may be puffed or dusted onto the affected area.

The rate of application of the active ingredient will depend upon the severity and the surface area of the disorder to be treated and repeated applications may be made at intervals during the day, e.g. from 1 to 6 times, and preferably twice, a day. The active ingredient may be applied prophylactically, but is more usually applied to an area which is already affected.

The compounds of formula I, and the pharmaceutically acceptable derivatives thereof find use in the treatment of various disorders in mammals, notably man, cats, dogs and horses.

According to the invention therefore we also provide a method for the treatment or prevention of a condition, in a mammal, e.g. man, cats, dogs and horses, which condition involves skin mast cells and/or delayed (cellular) hypersensitivity reactions, which method comprises administering an effective amount of a compound of formula I, or of a pharmaceutically acceptable derivative thereof, as active agent, to a mammal having, or susceptible to, such a condition.

Specific conditions in man and other animals which can be treated by the method of the invention include contact dermatitis to a specific allergen, e.g. nickel, chromates, synthetic resins, applied medicaments and other chemicals (Rook A., Wilkinson D. S. and Ebling F. J. S. 1972 Textbook of Dermatology 2nd Edition Blackwell, Oxford Chapters 14 and 15). Other conditions which can be treated by the method of this invention are those having as a component a delayed (cellular) hypersensitivity, for example autoallergic conditions, in particular thyroiditis, glomerular nephritis, adrenalitis, encephalomyelitis (post rabies vaccination), systemic lupus erythrematosis, rheumatoid arthritis, myasthena gravis, polymyositis, ulcerative colitis, Crohn's disease, pemphigus, homograft rejection following the transplantation of tissues and organs; certain infectious diseases, in particular tuberculosis, brucellosis, staphylococcal disease, streptococcal disease and delayed allergy to toxins and vaccines. (Clinical Aspects of Immunology, (3rd Edition 1975), Eds. P. G. H. Gell, P. R. A. Coombs, P. J. Lachmann, Chaps. 25, 28 and 35).

Dermatoses which can be treated include contact sensitivity, e.g. to chromium, nickel or an antibiotic, eczemas, drug eruptions, psoriasis, dermatitis herpetiformis, atopic dermatitis, apthous ulcers, Behçet's syndrome, pemphigus, urticaria, urticaria pigmentose, the ulcers of Crohn's disease, pyoderma gangrenosum and chronic skin ulcers, notably those affecting man in tropical climates. The active agent is of particular use in the treatment of atopic eczema in man. When pemphigus, apthous ulcers or Behçet's syndrome are to be treated the active agent may be applied to the mucous membrane. However we prefer not to apply the active agent to the mucous membranes.

The amount of the active agent to be administered will of course vary with the condition to be treated, the animal or patient to be treated, the particular derivative used and the mode of administration. However in the tests set out in Examples A and B we have found that generally satisfactory results can be achieved when the active agent is administered at a dosage of from about 10 to 100, and more preferably 10 to 75 mg per kg of animal body weight. For man the indicated daily dosage is in the range of from 1 mg to 3500 mg preferably 1 mg to 3000 mg and more preferably from 1 mg to 600 mg, which may be administered in divided doses from 1 to 6 times a day. When treating a skin condition the active agent is preferably administered topically, but may also be administered orally or by injection. When administering the active ingredient topically, e.g. as an ointment, the dosage is difficult to control, but will depend in general on the size and condition of the area to be treated.

The compositions of the invention may be set in the following decreasing order of importance: ointments, oil in water creams, water in oil creams, fatty alcohol/glycol bases, liniments and lotions and dusting powders.

Typical formulations of the compounds of formula I for application to the skin are illustrated by the following Examples:

EXAMPLE 1

| Ointment | |
|---|---|
| Compound of formula I | 10% w/v |
| Liquid paraffin BP | 10% w/v |
| Wool Fat BP | 10% w/v |
| White Soft Paraffin BP | 70% w/v |

EXAMPLE 2

| Water Miscible Ointment | |
|---|---|
| Compound of formula I | 10% w/v |
| Polyethylene glycol 400 | 40% w/v |
| Polyethylene glycol 4,000 | 50% w/v |

EXAMPLE 3

| Aqueous Cream | |
|---|---|
| Compound of formula I | 5% w/v |
| Emulsifying Ointment BP | 30% w/v |
| Chlorocresol | 1% w/v |
| Purified Water | 64% w/v |

EXAMPLE 4

| Oily Cream | |
|---|---|
| Compound of formula I | 10% w/v |
| Wool alcohols BP | 3% w/v |
| Hard paraffin BP | 12% w/v |
| White Soft Paraffin BP | 10% w/v |

| -continued | |
|---|---|
| Oily Cream | |
| Liquid Paraffin BP | 30% w/v |
| Purified Water | 35% w/v |

EXAMPLE 5

| Lotion (Aqueous) | |
|---|---|
| Compound of formula I | 10% w/v |
| Glycerol | 20% w/v |
| Alcohol (95%) | 20% w/v |
| Sodium Carboxymethyl Cellulose | 1% w/v |
| Purified Water | 49% w/v |

EXAMPLE 6

| Lotion (Oily) | |
|---|---|
| Compound of formula I | 15% w/v |
| Arachis Oil | 85% w/v |

EXAMPLE 7

| Gel | |
|---|---|
| Compound of formula I | 0.1% w/w |
| 'Carbopol' 934 | 1.5% w/w |
| Triethylamine | 0.46% w/w |
| Propylene glycol | 31.34% w/w |
| Distilled water | 66.6% w/w |

EXAMPLE 8

| Dusting Powder | |
|---|---|
| Compound of formula I | 10% w/v |
| Zinc Oxide | 25% w/v |
| Purified Talc | 10% w/v |
| Sterilisable Maize Starch | 55% w/v |

EXAMPLE 9

| Fatty alcohol/glycol base | |
|---|---|
| Compound of formula I | 10% w/v |
| Stearyl alcohol | 27% w/v |
| Propylene Glycol | 63% w/v |

The compound of formula I is typically present in the above formulations in from 0.1 to 10% by weight, notably 0.5 to 5%.

EXAMPLE 10

| Compound of formula I | 4.0% w/w |
|---|---|
| White soft paraffin BP | 81.0% w/w |
| Liquid paraffin BP | 10.0% w/w |
| Hard paraffin BP | 5.0% w/w |

EXAMPLE 11

| Compound of formula I | 4.0% w/w |
|---|---|
| Purified water | q.s. |
| Base to | 100% w/w |
| Base: | |
| Polyethylene glycol 400 | 5.0% w/w |
| White soft paraffin BP | 80.0% w/w |
| Liquid paraffin BP | 10.0% w/w |
| Hard paraffin BP | 5.0% w/w |

The compound of formula I is typically present in the formulations of Examples 9 and 10 in an amount of from 0.01 to 10% by weight and preferably from 0.5 to 5% by weight.

EXAMPLE 12

Ointment formulations were prepared by mixing the compound of formula I with a petroleum jelly base to give ointments containing 0.5 to 5% by weight of the compound of formula I. These ointments were applied to patients suffering from eczemas, notably atopic aczema, or contact sensitivity to a metal by smearing the ointments on to the affected areas of the skin from 2 to 4 times a day.

EXAMPLE A

Mouse Contact Sensitivity

Mice were sensitised by application of 100μ L 3% 2-phenyl-4-ethoxymethylene-oxazolone in acetone to the shaved abdomen. The mice were challenged seven days later by application of 15μ L 3% 2-phenyl-4-ethoxymethylene-oxazolone to one ear, and the degree of contact sensitivity assessed by measuring an increase in ear thickness 24h after challenge. The effect of the sodium salt of a compound of formula I on the reaction was assessed by dosing groups of mice with from 10 to 100 mg/kg of the compound intraperitoneally 1h before challenge. Up to 95% inhibition of the reaction was observed.

EXAMPLE B

Guinea Pig Delayed Hypersensitivity

Guinea pigs were sensitised with 0.4 ml Freunds complete adjuvant containing 1 mg/ml *M. tubercolosis*. The guinea pigs were challenged 14 days later by intradermal injection of 10μ g tuberculin purified protein derivative and the indurated, erythematous reactions quantitated at 24h by measuring increases in skin thickness and reaction diameter. The effect of the sodium salt of a compound of formula I was assessed by dosing groups of sensitised animals with 25 and 50 mg/kg of the compound given intraperitoneally as divided doses one hour before and 1 to 5 hours after challenge. Up to 75% inhibition of the reaction was observed.

EXAMPLE C

Mouse Contact Sensitivity - Topical Application

Mice were sensitised by application of 100μ L 3% 2-phenyl-4-ethoxymethylene-oxazalone in acetone to the shaved abdomen. The mice were challenged seven days later by application of 15μ L 3% 2-phenyl-4-ethoxymethylene-oxazalone to one ear, and the degree of contact sensitivity assessed by measuring an increase in ear thickness 24H after challenge. The effect of the sodium salt of a compound of formula I on the reaction was assessed by dosing groups of mice with from 8 to 10 mg of a gel containing 0.5% or 1.0% by weight of the sodium salt to one ear, the other ear being treated with the same amount of gel containing no active ingredient. The gel was applied either immediately after or one hour after challenge. Up to 80% inhibition of the reaction was observed.

We claim:

1. A pharmaceutical composition suitable for application to the skin for treatment of a condition in a mammal involving skin mast cells and/or delayed cellular hypersensitivity reaction, said composition comprising a pharmaceutical carrier acceptable on the skin of said mammal and, as active ingredient, an effective amount of a compound having the formula

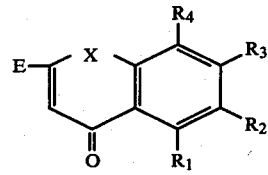

in which
   $R_1$ represents hydroxy,
   an adjacent pair of $R_2$, $R_3$ and $R_4$ form a $-(CH_2)_4-$ chain, and the remaining substituent $R_2$ or $R_4$ represents alkyl C 1 to 9,
   E represents a $-COOH$ group, and
   X represents oxygen,
   or a pharmaceutically acceptable salt, ester or amide thereof.

2. A composition according to claim 1, wherein $R_2$ and $R_3$ together form the $-(CH_2)_4-$ chain.

3. A composition according to claim 2, wherein $R_4$ is alkyl C 2 to 4.

4. A composition according to claim 1 wherein the active ingredient is selected from 7,8,9,10-Tetrahydro-5-hydroxy-4-oxo-6-propyl-4H-naphtho[2,3,-b]pyran-2-carboxylic acid, or a pharmaceutically acceptable salt thereof.

5. A composition according to claim 1, wherein the active ingredient is 6,7,8,9-tetrahydro-5-hydroxy-4-oxo-10-propyl-4H-naphtho[2,3-b]pyran-2-carboxylic acid, or a pharmaceutically acceptable salt thereof.

6. A composition according to claim 1 in the form of an ointment cream, lotion, liniment, paste, gel, emulsion, dusting powder, or solid carrier to which the active ingredient has been applied.

7. A composition according to claim 1 in the form of an ointment comprising a waxy, fatty, protein or paraffin base having the active ingredient dispersed therein.

8. A composition according to claim 7, wherein the base comprises from 70 to 90% by weight of a white or yellow soft paraffin, from 5 to 15% by weight of a liquid paraffin and from 0 to 12% by weight of a hard paraffin.

9. A composition according to claim 1, wherein the active ingredient is present in an amount of from 0.1 to 20% by weight of the total composition.

10. A composition according to claim 9, wherein the active ingredient is present in an amount of from 0.1 to 10% by weight of the total composition.

11. A composition according to claim 10, wherein the active ingredient is present in an amount of from 0.3 to 5% by weight of the total composition.

12. A method for the treatment of a condition in a mammal, which condition involves skin mast cells and/or a delayed (cellular) hyersensitivity reaction, which method comprises administering an effective amount of a composition of claim 1 to a mammal having such a condition.

13. The method of claim 12 in which said composition is applied topically to the skin of said mammal.

* * * * *